United States Patent
Flanagan (10) Patent No.: US 10,823,673 B2
(45) Date of Patent: Nov. 3, 2020

(54) DUAL FUNCTION FLUOROMETER-ABSORBANCE SENSOR

(71) Applicant: YSI, INC., Yellow Springs, OH (US)

(72) Inventor: Kevin Riley Flanagan, Yellow Springs, OH (US)

(73) Assignee: YSI, INC., Yellow Springs, OH (US)

(*) Notice: Subject to any disclaimer, the term of this patent is extended or adjusted under 35 U.S.C. 154(b) by 380 days.

(21) Appl. No.: 15/820,908

(22) Filed: Nov. 22, 2017

(65) Prior Publication Data

US 2018/0156730 A1   Jun. 7, 2018

Related U.S. Application Data

(60) Provisional application No. 62/425,695, filed on Nov. 23, 2016.

(51) Int. Cl.
   *G01N 21/64* (2006.01)
   *G01N 33/18* (2006.01)
   (Continued)

(52) U.S. Cl.
   CPC ............ *G01N 21/64* (2013.01); *G01J 3/42* (2013.01); *G01J 3/4406* (2013.01); *G01N 21/17* (2013.01);
   (Continued)

(58) Field of Classification Search
   None
   See application file for complete search history.

(56) References Cited

U.S. PATENT DOCUMENTS

| | | |
|---|---|---|
| 3,666,362 A | 5/1972 | Chance |
| 3,920,334 A | 11/1975 | Steichen et al. |

(Continued)

FOREIGN PATENT DOCUMENTS

WO     9614569 A2     5/1996

OTHER PUBLICATIONS

"Aqualog water quality measurements made easy," Horiba Scientific brochure, horiba.com, printed Dec. 2016. http://www.horiba.com/fileadmin/uploads/Scientific/Documents/Fluorescence/Aqualog-Nov13.pdf.

(Continued)

*Primary Examiner* — Jill A Warden
*Assistant Examiner* — Brittany I Fisher
(74) *Attorney, Agent, or Firm* — Ware, Fressola, Maguire & Barber LLP (57) ABSTRACT

A dual function fluorometer-absorbance sensor features an absorbance-based sensor configured to receive one part of an optical signal transmitted through a body of water of interest along an optical beam transmission path, and determine absorbance-based sensor signaling containing information about an absorbance of the optical signal by one or more absorbance species of interest present in the body of water; and a fluorescence-based sensor configured to receive another part of the optical signal transmitted through the body of water of interest along a corresponding optical beam transmission path that is perpendicular to the optical beam transmission path, and determine fluorescence-based sensor signaling containing information about a fluorescence transmitted by one or more fluorophore species of interest present in the body of water.

16 Claims, 3 Drawing Sheets

(51) Int. Cl.
*G01J 3/42* (2006.01)
*G01N 21/17* (2006.01)
*G01J 3/44* (2006.01)
*G02B 5/20* (2006.01)

(52) U.S. Cl.
CPC ......... *G01N 21/643* (2013.01); *G01N 21/645* (2013.01); *G01N 33/18* (2013.01); *G02B 5/20* (2013.01); *G01N 2021/174* (2013.01); *G01N 2021/6419* (2013.01); *G01N 2021/6491* (2013.01); *G01N 2201/0627* (2013.01)

(56) References Cited

U.S. PATENT DOCUMENTS

| | | | |
|---|---|---|---|
| 4,440,497 A | | 4/1984 | Carey et al. |
| 4,488,814 A | | 12/1984 | Johnson |
| 4,867,559 A | | 9/1989 | Bach |
| 4,927,265 A | | 5/1990 | Brownlee |
| 4,945,245 A | | 7/1990 | Levin |
| 5,929,453 A | * | 7/1999 | Andrews .............. G01N 21/645 250/461.1 |
| 6,236,456 B1 | | 5/2001 | Giebeler et al. |
| 6,280,703 B1 | | 8/2001 | Combs et al. |
| 7,209,223 B1 | | 4/2007 | Hull et al. |
| 7,855,780 B1 | | 12/2010 | Djeu |
| 8,901,513 B2 | | 12/2014 | Gilmore et al. |
| 8,906,698 B2 | | 12/2014 | Croud et al. |
| 2002/0193672 A1 | | 12/2002 | Walsh et al. |
| 2005/0264803 A1 | | 12/2005 | Jones |
| 2008/0174767 A1 | * | 7/2008 | Leonard ............. G01N 21/6452 356/73 |
| 2011/0242539 A1 | * | 10/2011 | Christensen .......... G01J 1/0271 356/440 |
| 2012/0228519 A1 | | 9/2012 | Gilmore et al. |
| 2016/0123882 A1 | * | 5/2016 | Gilmore .............. G01N 21/645 250/227.11 |

OTHER PUBLICATIONS

"Fluorescence Measurements For Evaluating The Application of Multivariate Analysis Techniques to Optically Thick Environments," Sandia Report, Sandia National Laboratories, Oct. 2010. http://prod.sandia.gov/techlib/access-control.cgi/2010/106571.pdf reichardt.pdf.

Holland, J.F., et al, "A unique computer centered instrument for simultaneous absorbance and fluorescence measurements," Analytical Chemistry, Jan. 1973, 45(1), pp. 145-153. http://pubs.acs.org/doi/abs/10.1021/ac60323a009.

Caslayska, J., et al, "Modification of a tunable UV-visible capillary electrophoresis detector for simultaneous absorbance and fluorescence detection: profiling of body fluids for drugs and endogenous compounds," Journal of Chromatography A, vol. 709, Issue 1, Aug. 11, 1995, pp. 147-156. http://www.sciencedirect.com/science/article/pii/0021967395001154.

* cited by examiner

Dual function fluorometer-absorbance sensor 10

An absorbance-based sensor (e.g., transmission optical receiver) 20 configured to receive an optical signal transmitted through a body of water of interest along an optical beam transmission path, and determine absorbance-based sensor signaling containing information about an absorbance of the optical signal by one or more absorbance species of interest present in the body of water.

A fluorescence-based sensor (e.g., emissions optical receiver) 30 configured to receive the optical signal transmitted through the body of water of interest along a corresponding optical beam transmission path that is perpendicular to the optical beam transmission path, and determine fluorescence-based sensor signaling containing information about a fluorescence transmitted by one or more fluorophore species of interest present in the body of water.

Signal processor 40 configured at least to:

receive the absorbance-based sensor signaling, and provide corresponding signaling containing information about the presence of the one or more absorbance species of interest in the body of water; and/or     receive the fluorescence-based sensor signaling, and provide further corresponding signaling containing information about the presence of the one or more fluorophore species of interest in the body of water.

Other signal processor circuits, circuitry, or components 42 that do not form part of the underlying invention, e.g., including input/output modules/modems, one or more memory modules (e.g., RAM, ROM, etc.), data, address and control busing architecture, etc.

Figure 3

DUAL FUNCTION FLUOROMETER-ABSORBANCE SENSOR

CROSS-REFERENCE TO RELATED APPLICATIONS

This application claims benefit to provisional patent application Ser. No. 62/425,695, filed 23 Nov. 2016, which is incorporated by reference in its entirety.

BACKGROUND OF THE INVENTION

1. Field of Invention

This invention relates to a sensor for measuring the quality of water; and more particularly, to an optical-based sensor for measuring the quality of water.

2. Description of Related Art

For optical-based water quality sensors, the two most common approaches are:

1) Fluorescence-based sensing, where an excitation light source (at some specified optical wavelength) is used to optically excite the water parameter of interest and re-emit optical light (at a longer optical wavelength) specific to the water parameter of interest. However, fluorescence-based sensors suffer from optical interferences, i.e. the presence of other competing fluorescence species that also fluoresce at the same target wavelength causing measurement ambiguity. Additionally, fluorescence sensors suffer an effect referred to as IFE (inner filter effect). IFE is a well-known and often measurement-inhibiting problem for fluorescence-based signals in general, significantly limiting their effective range. More specifically, in the region of significant IFE, the fluorescence signal becomes unresponsive to changes in the concentration of the fluorescence species (also known as a fluorophore) thereby rendering such measurements as erroneous.

2) Absorbance-based sensing, where the transmitted intensity of optical light is measured by optical sensor across an optical gap to determine the presence of the water quality parameter of interest that absorbs the optical light. However, typical absorbance-based sensors suffer from optical interferences, i.e. the presence of other competing species that also absorb causing measurement ambiguity.

In view of this, there is a need in the art for better optical-based water quality sensor.

SUMMARY OF THE INVENTION

In summary, the present invention can perform both, absorbance-based sensing and fluorescence based sensing; all in a single sensing body. Furthermore, this unique design allows for correction of one or all of the aforementioned shortcomings of the existing state of the art.

Two aspects of the present single invention are presented for clarity:

1) A fluorescence aspect of the present invention (fluorescence mode), generally setting forth the necessary electro-optical components and opto-mechanical layout to realize new techniques for hardware-based IFE correction and fluorescence interference correction.

2) An absorbance aspect of the present invention (absorbance mode), generally setting forth the necessary electro-optical components and opto-mechanical layout to realize new techniques for absorbance interference correction.

The Opto-Mechanical Layout

Regarding the opto-mechanical layout in general: The sensor disclosed herein differs from traditional fluorometers known in the art primarily in the details concerning the optical layout. The sensor embodiment according to the present invention contains single or multiple LEDs at specified excitation wavelengths, suitable to the fluorophore species or absorbance species of interest, and one or more optical receivers (e.g., photodetectors or optical spectrum analyzers) for transmission measurement of the excitation wavelength across a specified optical path, employing one or multiple optical bandpass filters, spectrally centered at the specified excitation wavelengths. The second optical receiver (or multiple receivers) is located perpendicular to the optical beam path, employing one or more optical bandpass filters spectrally centered at one or more specified fluorescence emission wavelengths, suitable to the fluorophores of interest, e.g., consistent with that shown in the drawing of this patent application.

In the fluorescence mode, the perpendicular optical receiver (e.g., a fluorescence receiver perpendicular to the transmission path) is the signal of interest being used primarily to measure fluorescence, but can also be tailored to measure turbidity (i.e., the cloudiness of the water). In this context, the transmission receiver(s) which is in-line with the excitation beam path, will be used to correct for IFE as follows: With access to both, the absorption signal (e.g., achieved through the transmission signal across an optical gap) and fluorescence signal (e.g., perpendicular to the excitation path), a simple ratio of the two signals can be performed in real time within the sensor to produce a third, IFE corrected signal. This IFE correction enhances (e.g., linearizes the response) and greatly extends the useful range of fluorescence detection. There is no known prior art associated with this form of IFE correction which is hardware-based (e.g., and experimentally confirmed) that can be done on the fly (e.g., in the field), as opposed to contemporary methods known in the prior art which rely on time consuming post-processing of the data in a laboratory environment. Furthermore, the capability of using multiple LEDs and multiple optical receivers allows for simultaneous detection and correction of multiple fluorescence species; all with IFE correction.

In the absorbance mode, the transmission receiver is the signal of interest being used primarily to measure absorbance, which is derived from the transmission signal. The capability of using multiple LEDs and multiple optical receivers allows for simultaneous correction of multiple interfering absorbance/fluorescence and scattering (turbidity) species. Absorbance corrections are common practice and are typically performed through absorbance measurements using a transmission optical receiver. However, the additional information provided by fluorescence or turbidity signals (perpendicular to excitation path) can greatly enhance optical interference correction capabilities. There is no known prior art associated with employing both, transmission and perpendicular signal capture to achieve correction, of which the inventor is aware.

In conclusion, many companies make fluorometers, and many other companies make absorbance sensors, but none make a dual sensor scenario (absorbance+fluorescence) in a single sensing embodiment. Furthermore, no company offers a hardware-based IFE correction for fluorescence measurements in a single sensing embodiment, of which the inventor is aware.

Specific Embodiments

According to some embodiments, the present invention may include, or take the form of, a dual function fluorometer-absorbance sensor, featuring an absorbance-based sensor and a fluorescence-based sensor.

The absorbance-based sensor may be configured to receive one part of an optical signal transmitted through a body of water of interest along an optical beam transmission path, and determine absorbance-based sensor signaling containing information about an absorbance of the optical signal by one or more absorbance species of interest present in the body of water.

The fluorescence-based sensor may be configured to receive another part of the optical signal transmitted through the body of water of interest along a corresponding optical beam transmission path that is perpendicular to the optical beam transmission path, and determine fluorescence-based sensor signaling containing information about a fluorescence transmitted by one or more fluorophore species of interest present in the body of water.

The dual function fluorometer-absorbance sensor may include one or more of the following additional features:

The dual function fluorometer-absorbance sensor may include an excitation LED optical arrangement for transmitting one or more optical beams having one or more specific excitation wavelengths suitable to determine the one or more absorbance and/or fluorophore species of interest. By way of example, the excitation LED optical arrangement may include one or more excitation LEDs for providing the one or more optical beams having the one or more specific excitation wavelengths. The excitation LED optical arrangement may also include one or more excitation filters for filtering the one or more optical beams having the one or more specific excitation wavelengths.

The absorbance-based sensor may include a transmission filter configured to filter the optical signal transmitted through the body of water of interest along the optical beam transmission path, and provide a transmission filtered optical signal containing information about a filtered absorbance of the optical signal by the one or more absorbance species of interest present in the body of water. The absorbance-based sensor may also include a transmission optical receiver configured to receive the transmission filtered optical signal, and provide the absorbance-based sensor signaling containing information about the absorbance of the optical signal by the one or more absorbance species of interest present in the body of water.

The fluorescence-based sensor may include a fluorescence emission filter configured to receive the optical signal transmitted through the body of water of interest along the corresponding optical beam transmission path that is perpendicular to the optical beam transmission path, and provide a fluorescence emission filtered optical signal containing information about a filtered fluorescence transmitted by the one or more fluorophore species of interest present in the body of water. The fluorescence-based sensor may also include a fluorescence emission optical receiver configured to receive the fluorescence emission filtered optical signal, and provide the fluorescence-based sensor signaling containing information about the fluorescence transmitted by the one or more fluorophore species of interest present in the body of water.

The dual function fluorometer-absorbance sensor may include a signal processor configured to:
- receive the absorbance-based sensor signaling, e.g., provided from the absorbance-based sensor, and provide corresponding signaling containing information about the presence of the one or more absorbance species of interest in the body of water; and/or
- receive the fluorescence-based sensor signaling, e.g., provided from the fluorescence-based sensor, and provide further corresponding signaling containing information about the presence of the one or more fluorophore species of interest in the body of water.

The signal processor may be configured to correct an inner filter effect (IFE) error in the fluorescence-based sensor signaling based upon the absorbance-based sensor signaling. The signal processor may be configured to correct the IFE error, e.g. by using a simple ratio of the fluorescence-based sensor signaling and the absorbance-based sensor signaling, and provide an IFE corrected fluorescence-based sensor signal.

The Method

According to some embodiments, the present invention may include a method for measuring the quality of water, featuring:
- configuring an absorbance-based sensor of a dual function fluorometer-absorbance sensor to receive one part of an optical signal transmitted through a body of water of interest along an optical beam transmission path, and determine absorbance-based sensor signaling containing information about an absorbance of the optical signal by one or more absorbance species of interest present in the body of water; and
- configuring a fluorescence-based sensor of the dual function fluorometer-absorbance sensor to receive the optical signal transmitted through the body of water of interest along a corresponding optical beam transmission path that is perpendicular to the optical beam transmission path, and determine fluorescence-based sensor signaling containing information about a fluorescence transmitted by one or more fluorophore species of interest present in the body of water.

Moreover, the method may also include configuring the dual function fluorometer-absorbance sensor with a signal processor to:
- receive the absorbance-based sensor signaling, and provide corresponding signaling containing information about the presence of the one or more absorbance species of interest in the body of water; and/or
- receive the fluorescence-based sensor signaling, and provide further corresponding signaling containing information about the presence of the one or more fluorophore species of interest in the body of water.

The method may also include one or more of the features set forth above.

Computer-Readable Storage Medium

According to some embodiments of the present invention, the present invention may also take the form of a computer-readable storage medium having computer-executable components for performing the steps of the aforementioned method. The computer-readable storage medium may also include one or more of the features set forth above.

Advantages

One advantage of the present invention is that it addresses the aforementioned limitations in the prior art techniques by providing the IFE correction that can be done on the fly (e.g., in the field), as well as simultaneous detection and correction of multiple fluorescence species, all with the IFE correction.

Another advantage of the present invention is that it addresses the aforementioned limitations in the prior art techniques by allowing simultaneous correction of multiple interfering absorbance/fluorescence and scattering (turbidity) species, which greatly enhances optical interference correction capabilities.

It is noted that the spirit of this invention is not restricted to an identification of any particular fluorescent or absorbance species, but rather encompasses any and all fluorescence and absorbance species which are capable of optical transmission, absorbance and subsequent fluorescence if applicable (i.e., not all absorbance species fluoresce, but all fluorescence species absorb).

BRIEF DESCRIPTION OF THE DRAWING

The drawing, which are not necessarily drawn to scale, includes FIGS. 1-3, as follows:

FIG. 3 is a block diagram of a dual function fluorometer-absorbance sensor, e.g., having an absorbance-based sensor, a fluorescence-based sensor and a signal processor for performing signal processing functionality, according to some embodiments of the present invention.

To reduce clutter in the drawing, each Figure in the drawing does not necessarily include every reference label for every element shown therein.

DETAILED DESCRIPTION OF BEST MODE OF THE INVENTION

Figure 1:
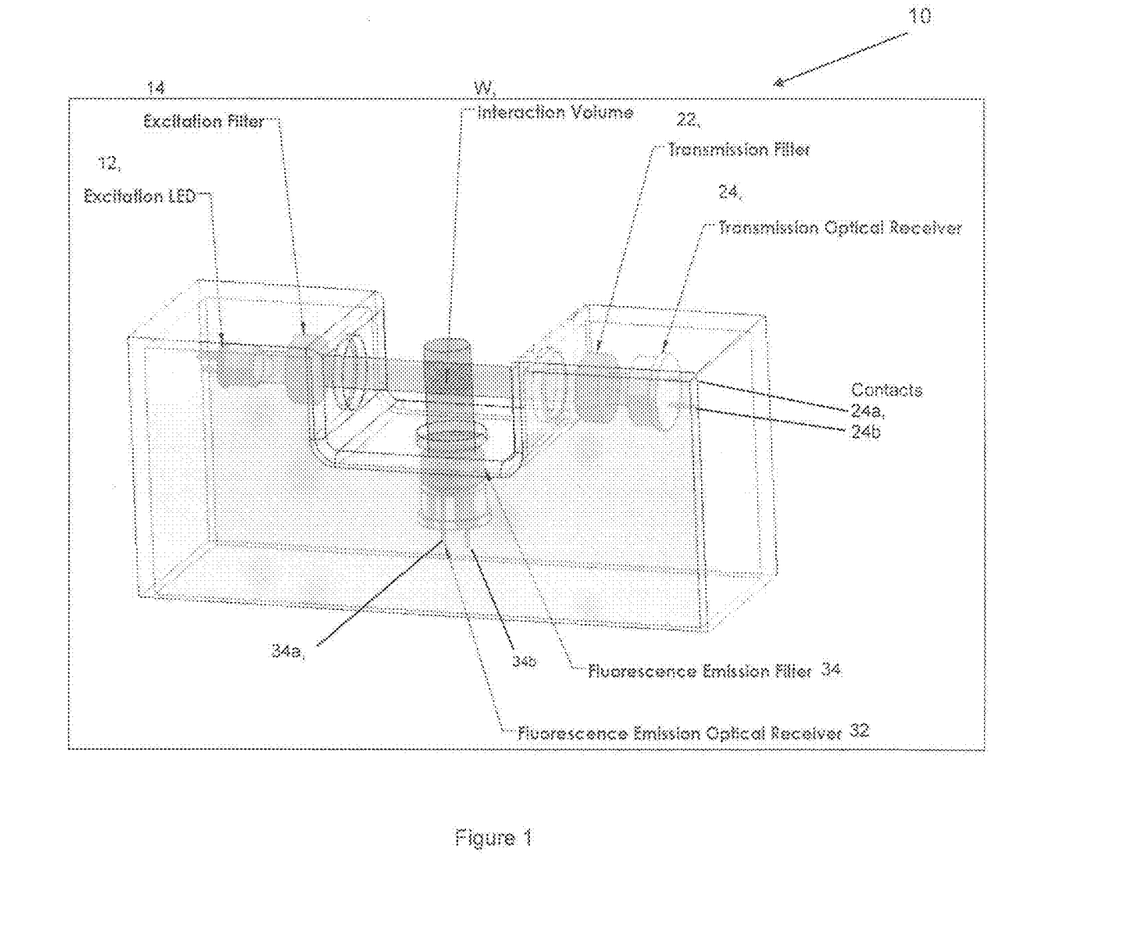
FIG. 1 is a diagram of a dual function fluorometer-absorbance sensor, according to some embodiments of the present invention.

FIG. 1

By way of example, according to some embodiments, the present invention may include, or take the form of, a dual function fluorometer-absorbance sensor generally indicated as 10, featuring an absorbance-based sensor 20 (FIG. 3) and a fluorescence-based sensor 30 (FIG. 3).

The absorbance-based sensor 20 may be configured to receive one part of an optical signal generally indicated as O transmitted through a body of water W of interest along an optical beam transmission path generally indicated as P1, and determine absorbance-based sensor signaling containing information about an absorbance of the optical signal O by one or more absorbance species of interest present in the body of water W.

The fluorescence-based sensor 30 may be configured to receive another part of the optical signal O transmitted through the body of water W of interest along a corresponding optical beam transmission path P2 that is perpendicular to the optical beam transmission path P1, and determine fluorescence-based sensor signaling containing information about a fluorescence transmitted by one or more fluorophore species of interest present in the body of water W.

The Excitation LED Optical Arrangement 12, 14

The dual function fluorometer-absorbance sensor 10 may include an excitation LED optical arrangement 12, 14 for transmitting the optical signal O, e.g., in the form of one or more optical beams having one or more specific excitation wavelengths suitable to determine the one or more absorbance and/or fluorophore species of interest. By way of example, the excitation LED optical arrangement may include one or more excitation LEDs 12 for providing the one or more optical beams having the one or more specific excitation wavelengths. Moreover, the excitation LED optical arrangement may include one or more excitation filters 14 for filtering the one or more optical beams having the one or more specific excitation wavelengths. Excitation LEDs and filters like elements 12, 14 are known in the art, and the scope of the invention is not intended to be limited to any particular type or kind thereof either now known or later developed in the future.

Absorbance Transmission Filter 22 and Transmission Optical Receiver 24

The absorbance-based sensor 20 may include a transmission filter generally indicated as 22 and transmission optical receiver generally indicated as 24. The transmission filter 22 may be configured to filter the optical signal O transmitted through the body of water W of interest along the optical beam transmission path P1, and provide a transmission filtered optical signal containing information about a filtered absorbance of the optical signal O by the one or more absorbance species of interest present in the body of water O. The transmission optical receiver 22 may be configured to receive the transmission filtered optical signal, and provide the absorbance-based sensor signaling, e.g., provided via contacts 24a, 24b, containing information about the absorbance of the optical signal by the one or more absorbance species of interest present in the body of water. Transmission filters and optical receiver like elements 22, 24 are known in the art, and the scope of the invention is not intended to be limited to any particular type or kind thereof either now known or later developed in the future.

Fluorescence Emission Filter and Emission Optical Receiver 32, 34

The fluorescence-based sensor 30 may include a fluorescence emission filter generally indicated as 32 and fluorescence emission optical receiver generally indicated as 34. The fluorescence emission filter 32 may be configured to receive the part of the optical signal transmitted through the body of water of interest along the corresponding optical beam transmission path P2 that is perpendicular to the optical beam transmission path P1, and provide a fluorescence emission filtered optical signal containing information about a filtered fluorescence transmitted by the one or more fluorophore species of interest present in the body of water. The fluorescence emission optical receiver 34 may be configured to receive the fluorescence emission filtered optical signal, and provide the fluorescence-based sensor signaling, e.g., via contacts 34a, 34b, containing information about the fluorescence transmitted by the one or more fluorophore species of interest present in the body of water. Fluorescence emission filter and emission optical receiver like elements 32, 34 are known in the art, and the scope of the invention is not intended to be limited to any particular type or kind thereof either now known or later developed in the future.

Figure 2:
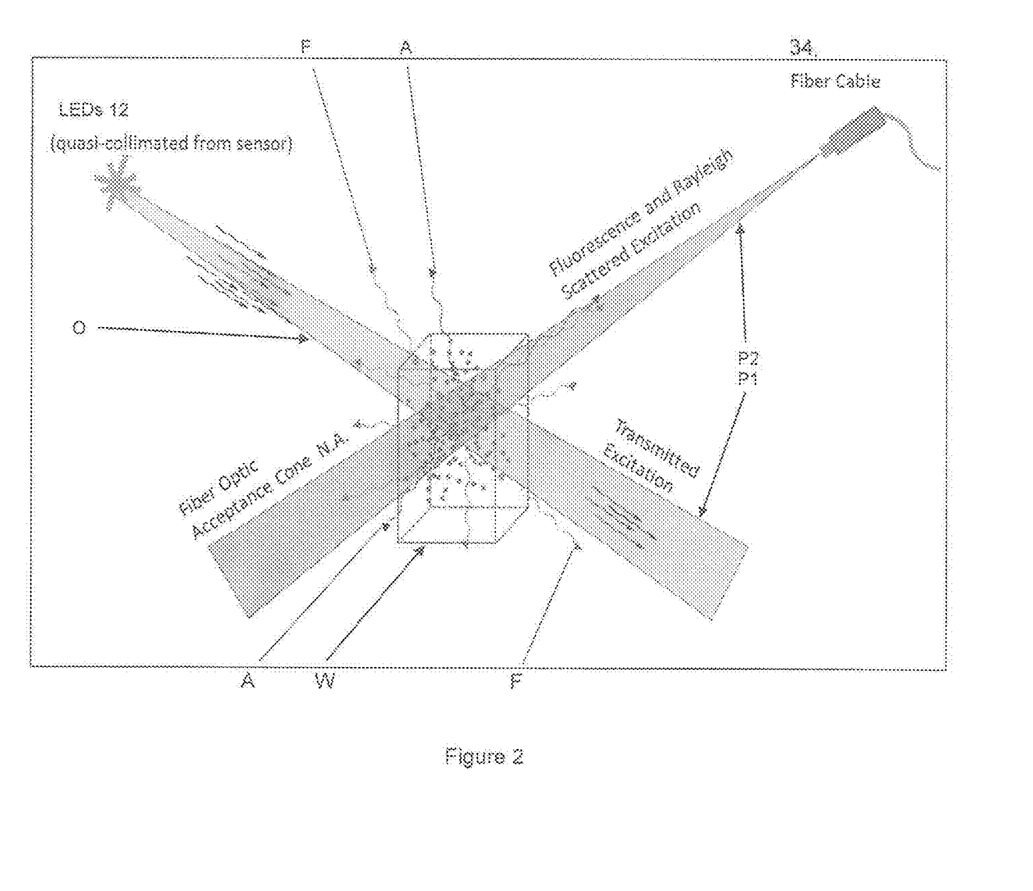
FIG. 2 is a diagram of an LED arrangement that transmits an optical signal through a body of water of interest along an optical beam transmission path, transmitted excitations being emitted, fluorescence and Rayleigh scatter excitations being emitted, both excitations/emissions for sensing perpendicular to one another, according to some embodiments of the present invention.

FIG. 2

FIG. 2 shows the optical signal transmitted by the one or more LEDs like element 12 through the body of water W of interest along the optical beam transmission path like P1, as well as the transmitted excitations generally indicated as A containing the absorbance of the optical signal O by the one or more absorbance species of interest present in the body of water W, and the fluorescence and Rayleigh scatter excitations generally indicated F containing the fluorescence transmitted by the one or more fluorophore species of interest present in the body of water W, e.g., for sensing along the paths P1, P2 that are perpendicular to one another. By way of example, the optical signal transmitted from the LED may be a quasi-collimated signal, as shown. By way of example, the optical receiver sensing the part of the optical signal having the fluorescence and Rayleigh scatter excitations F may include a fiber cable like element 34, as shown. FIG. 2 shows a fiber optic acceptance cone for receiving the the fluorescence and Rayleigh scatter excitations F.

FIG. 3

The dual function fluorometer-absorbance sensor 10 may also include a signal processor 40 configured to:
  receive the absorbance-based sensor signaling (e.g., like that provided from the contacts 24a, 24b of the transmission optical receiver 24), and provide corresponding signaling containing information about the presence of the one or more absorbance species of interest in the body of water W; and/or
  receive the fluorescence-based sensor signaling (e.g., like that provided from the contacts 34a, 34b of the fluorescence emission optical receiver 34), and provide further corresponding signaling containing information about the presence of the one or more fluorophore species of interest in the body of water.

The signal processor 40 may be configured to correct an inner filter effect (IFE) error in the fluorescence-based sensor signaling based upon the absorbance-based sensor signaling. For example, and by way of example, the signal processor may be configured to correct the IFE error by using a simple ratio of the fluorescence-based sensor signaling and the absorbance-based sensor signaling, and provide an IFE corrected fluorescence-based sensor signal.

Implementation of Signal Processing Functionality

By way of example, the functionality of the signal processor 40 may be implemented using hardware, software, firmware, or a combination thereof. In a typical software implementation, the signal processor 40 would include one or more microprocessor-based architectures having, e.g., at least one signal processor or microprocessor like element 40. One skilled in the art would be able to program with suitable program code such a microcontroller-based, or microprocessor-based, implementation to perform the signal processing functionality disclosed herein without undue experimentation.

For example, the signal processor 40 may be configured, e.g., by one skilled in the art without undue experimentation, to receive the absorbance-based sensor signaling, and provide corresponding signaling containing information about the presence of the one or more absorbance species of interest in the body of water, consistent with that disclosed herein.

For example, the signal processor 40 may be configured, e.g., by one skilled in the art without undue experimentation, to receive the fluorescence-based sensor signaling, and provide further corresponding signaling containing information about the presence of the one or more fluorophore species of interest in the body of water, consistent with that disclosed herein.

The scope of the invention is not intended to be limited to any particular implementation using technology either now known or later developed in the future. The scope of the invention is intended to include implementing the functionality of the signal processor(s) 40 as stand-alone processor, signal processor, or signal processor module, as well as separate processor or processor modules, as well as some combination thereof.

By way of example, the dual function fluorometer-absorbance sensor 10 may also include, e.g., other signal processor circuits or components generally indicated 42, including random access memory or memory module (RAM) and/or read only memory (ROM), input/output devices and control, and data and address buses connecting the same, and/or at least one input processor and at least one output processor, e.g., which would be appreciate by one skilled in the art.

By way of further example, the signal processor 40 and other signal processor circuits or components generally indicated 42 may include, or take the form of, some combination of a signal processor and at least one memory including a computer program code, where the signal processor and at least one memory are configured to cause the system to implement the functionality of the present invention, e.g., to respond to signaling received and to determine the corresponding signaling, based upon the signaling received.

Optical-to-Electrical Signal Conversion

As one skilled in the art would appreciate, techniques for converting sensed optical signaling into electrical signaling, e.g., for further signal processing, are known in the art, and the scope of the invention is not intended to be limited to any particular type or kind of technique either now known or later developed in the future.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:
1. A dual function fluorometer-absorbance sensor, comprising:
  an absorbance-based sensor that receives one part of an optical signal transmitted through a body of water of interest along an optical beam transmission path, and provides absorbance-based sensor signaling containing information about an absorbance of the optical signal by one or more absorbance species of interest present in the body of water;

a fluorescence-based sensor that receives another part of the optical signal transmitted through the body of water of interest along a corresponding optical beam transmission path that is perpendicular to the optical beam transmission path, and provides fluorescence-based sensor signaling containing information about a fluorescence transmitted by one or more fluorophore species of interest present in the body of water; and a signal processor that receives the absorbance-based sensor signaling and the fluorescence-based sensor signaling, determines an inner filter effect (IFE) error in the fluorescence-based sensor signaling in real time based upon a simple ratio of the fluorescence-based sensor signaling and the absorbance-based sensor signaling, and provides IFE-corrected fluorescence-based sensor signaling containing information about an IFE-correct fluorescence transmitted by the one or more fluorophore species of interest present in the body of water.

2. The dual function fluorometer-absorbance sensor according to claim 1, wherein the dual function fluorometer-absorbance sensor comprises an excitation LED optical arrangement that transmits one or more optical beams having one or more specific excitation wavelengths suitable to determine either the one or more absorbance species of interest, or the one or more fluorophore species of interest, or both the one or more absorbance species of interest and the one or more fluorophore species of interest.

3. The dual function fluorometer-absorbance sensor according to claim 2, wherein the excitation LED optical arrangement comprises one or more excitation LEDs that provides the one or more optical beams having the one or more specific excitation wavelengths.

4. The dual function fluorometer-absorbance sensor according to claim 3, wherein the excitation LED optical arrangement comprises one or more excitation filters that filters the one or more optical beams having the one or more specific excitation wavelengths.

5. The dual function fluorometer-absorbance sensor according to claim 1, wherein the absorbance-based sensor comprises a transmission filter that filters the optical signal transmitted through the body of water of interest along the optical beam transmission path, and provides a transmission filtered optical signal containing information about a filtered absorbance of the optical signal by the one or more absorbance species of interest present in the body of water.

6. The dual function fluorometer-absorbance sensor according to claim 5, wherein the absorbance-based sensor comprises a transmission optical receiver that receives the transmission filtered optical signal, and provides the absorbance-based sensor signaling containing information about the absorbance of the optical signal by the one or more absorbance species of interest present in the body of water.

7. The dual function fluorometer-absorbance sensor according to claim 1, wherein the fluorescence-based sensor comprises a fluorescence emission filter that receives the optical signal transmitted through the body of water of interest along the corresponding optical beam transmission path that is perpendicular to the optical beam transmission path, and provides a fluorescence emission filtered optical signal containing information about a filtered fluorescence transmitted by the one or more fluorophore species of interest present in the body of water.

8. The dual function fluorometer-absorbance sensor according to claim 7, wherein the fluorescence-based sensor comprises a fluorescence emission optical receiver that receives the fluorescence emission filtered optical signal, and provides the fluorescence-based sensor signaling containing information about the fluorescence transmitted by the one or more fluorophore species of interest present in the body of water.

9. A method for measuring the quality of water, comprising:

receiving with an absorbance-based sensor of a dual function fluorometer-absorbance sensor one part of an optical signal transmitted through a body of water of interest along an optical beam transmission path, and determining absorbance-based sensor signaling containing information about an absorbance of the optical signal by one or more absorbance species of interest present in the body of water;

receiving with a fluorescence-based sensor of the dual function fluorometer-absorbance sensor another part of the optical signal transmitted through the body of water of interest along a corresponding optical beam transmission path that is perpendicular to the optical beam transmission path, and determining fluorescence-based sensor signaling containing information about a fluorescence transmitted by one or more fluorophore species of interest present in the body of water; and receiving with a signal processor the absorbance-based sensor signaling and the fluorescence-based sensor signaling, determining an inner filter effect (IFE) error in the fluorescence-based sensor signaling in real time based upon a simple ratio of the fluorescence-based sensor signaling and the absorbance-based sensor signaling, and providing IFE-corrected fluorescence-based sensor signaling containing information about an IFE-corrected fluorescence transmitted by the one or more fluorophore species of interest present in the body of water.

10. The method according to claim 9, wherein the method comprises transmitting from the dual function fluorometer-absorbance sensor having an excitation LED optical arrangement one or more optical beams having one or more specific excitation wavelengths suitable to determine the one or more absorbance species of interest.

11. The method according to claim 10, wherein the method comprises providing from the excitation LED optical arrangement having one or more excitation LEDs the one or more optical beams having the one or more specific excitation wavelengths.

12. The method according to claim 11, wherein the method comprises filtering with the excitation LED optical arrangement having or more excitation filters the one or more optical beams having the one or more specific excitation wavelengths.

13. The method according to claim 9, wherein the method comprises filtering with the absorbance-based sensor having a transmission filter the optical signal transmitted through the body of water of interest along the optical beam transmission path, and providing a transmission filtered optical signal containing information about a filtered absorbance of the optical signal by the one or more absorbance species of interest present in the body of water.

14. The method according to claim 13, wherein the method comprises receiving with the absorbance-based sensor having a transmission optical receiver the transmission filtered optical signal, and providing the absorbance-based sensor signaling containing information about the absorbance of the optical signal by the one or more absorbance species of interest present in the body of water.

15. The method according to claim 9, wherein the method comprises receiving with the fluorescence-based sensor having a fluorescence emission filter the optical signal transmitted through the body of water of interest along the corresponding optical beam transmission path that is perpendicular to the optical beam transmission path, and providing a fluorescence emission filtered optical signal containing information about a filtered fluorescence transmitted by the one or more fluorophore species of interest present in the body of water.

16. The method according to claim 15, wherein the method comprises receiving with the fluorescence-based sensor having a fluorescence emission optical receiver the fluorescence emission filtered optical signal, and providing the fluorescence-based sensor signaling containing information about the fluorescence transmitted by the one or more fluorophore species of interest present in the body of water.

\* \* \* \* \*